United States Patent [19]
Peyser

[11] 3,947,690
[45] Mar. 30, 1976

[54] RADIATION LIMITING MEANS

[75] Inventor: Leonard F. Peyser, Briarcliff Manor, N.Y.

[73] Assignee: The Machlett Laboratories, Inc., Stamford, Conn.

[22] Filed: July 11, 1974

[21] Appl. No.: 487,501

[52] U.S. Cl.................................. 250/513; 250/511
[51] Int. Cl.² ........................................ G03B 41/16
[58] Field of Search..................... 250/511, 512, 513

[56] References Cited
UNITED STATES PATENTS

| | | | |
|---|---|---|---|
| 1,738,945 | 12/1929 | Brenbert | 250/512 |
| 1,909,118 | 5/1933 | Raab | 250/513 |
| 3,023,314 | 2/1962 | Hura | 250/439 |
| 3,163,762 | 12/1964 | Peyser | 250/512 |
| 3,304,427 | 2/1967 | Peyser | 250/512 |
| 3,448,270 | 6/1969 | Peyser | 250/513 |
| 3,609,370 | 9/1971 | Peyser | 250/511 |
| 3,829,701 | 8/1974 | Hura | 250/513 |

Primary Examiner—Alfred E. Smith
Assistant Examiner—B. C. Anderson
Attorney, Agent, or Firm—John T. Meaney; Joseph D. Pannone; Harold A. Murphy

[57] ABSTRACT

A radiation limiting shutter device including a hollow, frusto-pyramidal structure having relatively movable walls made of radiation absorbent material and defining an entrance aperture of a desired size, each of the walls comprising a frusto-triangular plate having serrated sloped edges which intermesh with similar sloped edges of respective adjacent plates forming the structure.

10 Claims, 5 Drawing Figures

RADIATION LIMITING MEANS

BACKGROUND OF THE INVENTION

This invention relates generally to radiation collimator devices and is concerned more particularly with an X-ray collimator having adjustable entrance shutter means which is sufficiently compact to operate within the recessed area of an X-ray generator port.

An X-ray generator usually comprises an oil-filled housing having therein an X-ray tube provided with an electron-emitting cathode and a spaced anode target. The cathode generally is disposed to direct a beam of electrons onto a small area, known as the "focal spot" area, of the anode with sufficient energy to generate X-rays in the target material. As a result, X-rays radiate from the focal spot area in all directions within the tube envelope. The useful portion of these X-rays pass, in the form of a conical beam, through an X-ray transparent window of a radially aligned port which is recessed in the wall of the housing. Thus, the focal spot area of the anode target ideally functions as a point source of the conical X-ray beam emanating from the port of the X-ray generator.

The X-ray beam may be directed, for example, through a selected region of a human patient for a limited interval of time, and impinge on an aligned surface area of a rectangular film. In this manner, the internal structure of the irradiated region may be reproduced on film for purposes of display and diagnostic study. However, in order to protect the patient from overexposure to X-radiation, it is required that the irradiated region of the patient be no larger than the effective area of the rectangular film. Accordingly, there may be mounted over the port of the X-ray generator a collimator housing having therein suitable X-ray absorbent shutter means for providing an adjustable exit aperture of the desired size. In this manner, the conical X-ray beam emanating from the port of the X-ray generator may be restricted by the collimator shutter means to the proper cross-sectional size and configuration for conforming to the effective area of the rectangular film.

The resulting image produced on the X-ray film by the collimated beam may not be sharply defined due to stray X-radiation generated in portions of the anode target outside of the focal spot area. In order to minimize the transmission of this off-focus radiation, the collimator may include an entrance aperture disposed as close as possible to the focal spot area of the anode target. Consequently, X-ray collimators of the prior art have been provided with entrance shutter means adapted to extend into the recessed port area of the X-ray generator. However, these prior art entrance shutter means generally operate inefficiently either by allowing an excessive amount of off-focus radiation to leak through, or by cutting off an excessive amount of useful X-radiation emanating from the focal spot area.

Therefore, it is advantageous and desirable to provide an X-ray collimator with adjustable entrance shutter means for efficiently limiting the passage of off-focus X-radiation while permitting the passage of X-radiation from an aligned X-ray source.

SUMMARY OF THE INVENTION

Accordingly, this invention provides a radiation shutter device comprising a hollow frusto-pyramidal structure having radiation absorbent walls which are movable relative to the axial centerline of the structure and define a radiation limiting entrance aperture, the walls having adjacent edge portions intermeshing with one another to minimize the leakage of off-focus radiation between the movable walls of the structure.

The frusto-pyramidal structure comprises a plurality of frusto-triangular plates angularly disposed with respect to one another, and inclined relative to the axial centerline of the structure. The base portions of the plates are pivotally supported and the opposing ends thereof define the radiation limiting entrance aperture. The frusto-triangular plates have respective sloped edges which are serrated and intermesh with serrated sloped edges of respective adjacent plates forming the structure. Each sloped edge of a respective frusto-triangular plate may be provided with a plurality of spaced arcuate teeth which are concentrically disposed with respect to the associated base corner of the plate. The frusto-triangular plates may be resiliently urged toward respective positions for defining a fully open entrance aperture, and may be cammed toward the axial centerline of the structure to define an entrance aperture of relatively smaller size. Thus, the described frusto-pyramidal shutter is especially well-suited for interfitting with a recessed port of an X-ray generator and may even be fixedly mounted in the port of the X-ray generator.

A preferred embodiment of this invention comprises an X-ray collimator device including a housing having protruding therefrom a frusto-pyramidal entrance shutter, which is adapted to extend within the recessed port area of an associated X-ray generator. Within the housing, the collimator may be provided with an X-ray beam collimating shutter comprising two orthogonally disposed pairs of opposing pivotal plates which define a rectangular exit aperture. The frusto-pyramidal entrance shutter may comprise four sloped walls, each wall being a frusto-triangular plate which is disposed in registration with one of the beam collimating plates within the housing and is movable therewith. Thus, the entrance aperture formed by the plates of the frusto-pyramidal shutter is adjustable in correspondence with the exit aperture formed by the plates of the beam collimating shutter.

BRIEF DESCRIPTION OF THE DRAWINGS

For a better understanding of this invention, reference is made in the following detailed description to the accompanying drawings wherein.

DESCRIPTION OF THE PREFERRED EMBODIMENT

Figure 1:
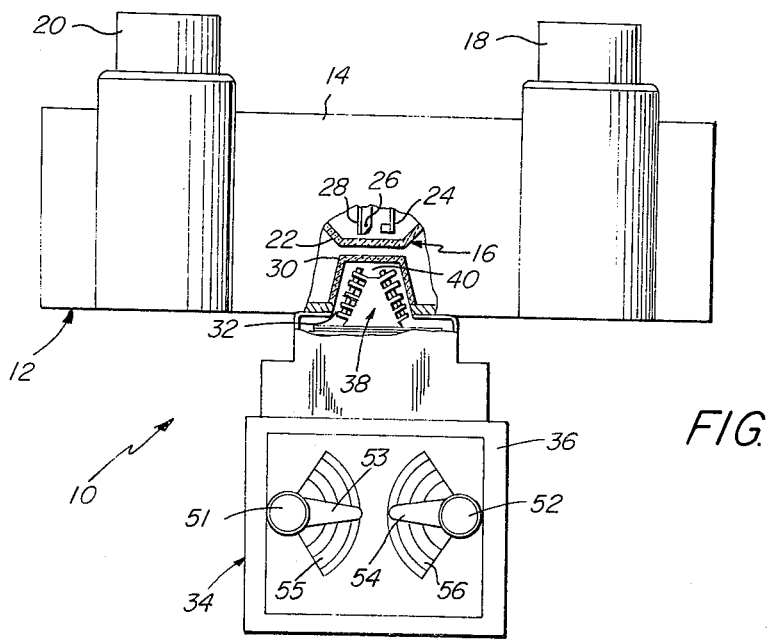
FIG. 1 is a pictorial view of a collimator embodying this invention and attached in operative relationship to an X-ray generator.

Referring more particularly to the drawings wherein like characters of reference designate like parts, there is shown in FIG. 1 an X-ray apparatus 10 which includes an X-ray generator 12 having a hollow cylindrical casing 14 wherein an X-ray tube 16 is longitudinally disposed. Casing 14 generally is filled with a dielectric coolant, such as oil, for example, and is provided with externally extending cable terminals 18 and 20, respectively, whereby electrical potentials are applied to the electrodes of X-ray tube 16.

Within the envelope 22 of X-ray tube 16, an electron emitting cathode 24 is disposed to direct a beam of electrons onto a small focal spot area 26 of an anode target 28, which may be of the rotating type, for example. The electrons impinge on the focal spot area 26 with sufficient energy to generate X-rays which radiate therefrom in all directions. Consequently, the casing 14 generally is lined with a suitable material, such as lead, for example, for absorbing a major portion of the unused X-rays emanating from the focal spot area 26.

The useful portion of the X-rays, thus produced, radiate from focal spot area 26 in a conical-shaped beam which passes through an X-ray transparent window 30 of a radially aligned port 32. The port 32 is cup-shaped and recessed in the cylindrical wall of casing 14 such that the window 30 is disposed in close proximity to the focal spot area 26 of anode target 28. Thus, the focal spot area 26 functions as a point source of the conical X-ray beam passing through the adjacent window 30 of port 32. However, off-focus X-radiation generated in portions of the anode target 28 outside of the focal spot area 26 also passes through the window 30 of port 32, usually at an angle with the axial centerline of the conical X-ray beam emanating from focal spot area 26.

Mounted over port 32, in a well-known manner, is an X-ray collimator 34 including a housing 36 having protruding therefrom an entrance shutter 38 of this invention, which is aligned with the focal spot area 26 of anode target 28. The entrance shutter 38 comprises a hollow frusto-pyramidal entrance structure having sloped walls which extend into the recessed area of port 32 and are adjustable with respect to the axial centerline of the structure. The sloped walls of entrance shutter 38 are made of X-ray absorbent material and define, in close proximity to the focal spot area 26, an entrance aperture 40 through which the conical X-ray beam emanating from focal spot area 26 passes to enter the housing 36 of collimator 34. However, the sloped walls of entrance shutter 38 also have intermeshing sloped edge portions whereby off-focus radiation is restricted from enteringg and passing through the collimator 34. Alternatively, the frusto-pyramidal shutter 38 of this invention, independently of the collimator 34, may be mounted in the port 32 of casing 14 to restrict the passage of off-focus X-radiation out of the X-ray generator 12.

Figure 2:
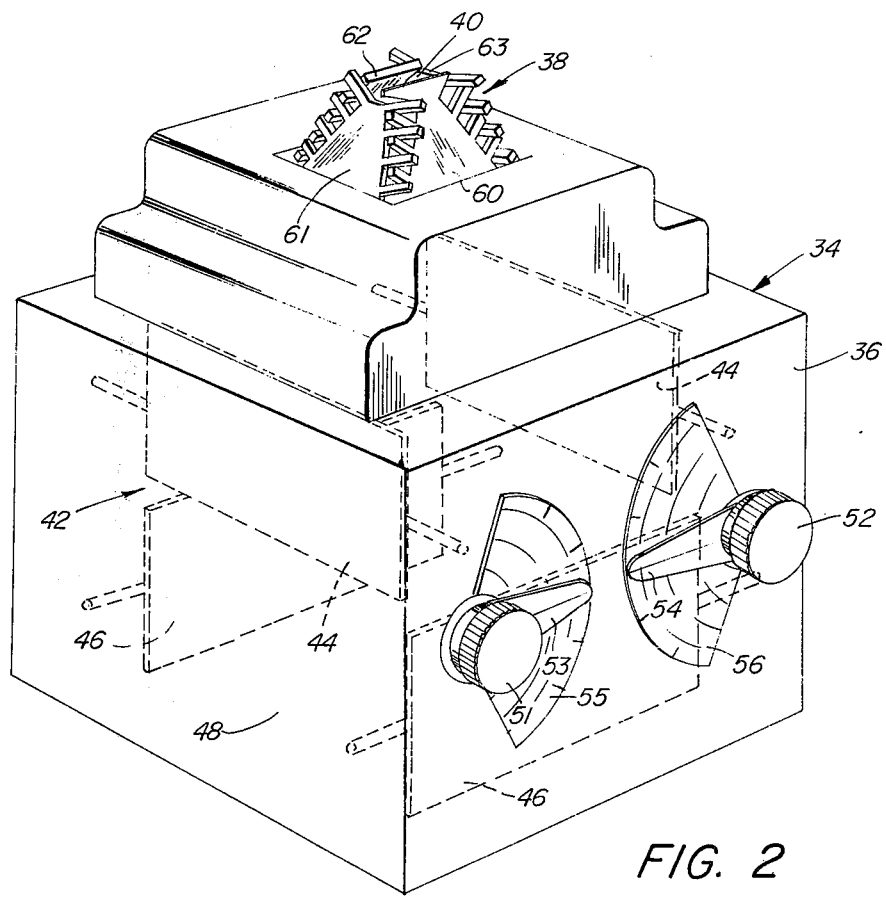
FIG. 2 is an isometric view of the collimator shown in FIG. 1.

As shown in FIG. 2, the collimator 34 includes a beam collimating shutter 42 suitably disposed within housing 36 for providing an emerging X-ray beam with a desired cross-sectional size and configuration. The beam collimating shutter 42 may comprise two orthogonally disposed pairs of opposing pivoted plates 44 and 46, respectively, which define a rectangular exit aperture 48. A beam collimating device of the described type is shown, for example, in U.S. Pat. No. 3,304,427 granted to the inventor and assigned to the assignee of this invention. As more fully disclosed therein, the pairs of plates 44 and 46 may be pivoted to provide a rectangular exit aperture 48 of a desired size by adjusting suitably connected knobs, 51 and 52, respectively, which are located on the front of housing 36. The knobs 51 and 52 carry respective pointers 53 and 54 which indicate on underlying scales, 55 and 56, respectively, the selected dimensions of rectangular exit aperture 48.

The entrance shutter 38 associated with the described beam collimating shutter 42 may comprise a hollow frusto-pyramidal structure having four sloped walls 60–63, respectively. The walls 60–63 comprise respective frusto-triangular plates of X-ray absorbent material, such as lead, for example, the smaller end portions of which converge toward the axial center line of the structure to form a rectangular entrance aperture 40. Each of the plates 60–63 is disposed in registration with a respective one of the beam collimating plates 44 and 46, and is movable simultaneously therewith to vary the entrance aperture 40 correspondingly with adjustment of the exit aperture 48. The plates 60–63 have respective sloped edge portions which are serrated and intermesh with similar sloped edge portions of adjacent plates forming the frusto-pyramidal structure. Thus, off-focus radiation is restricted from leaking between the movable plates 60–63, respectively, and entering the housing 36 of collimator 32.

Figure 3:
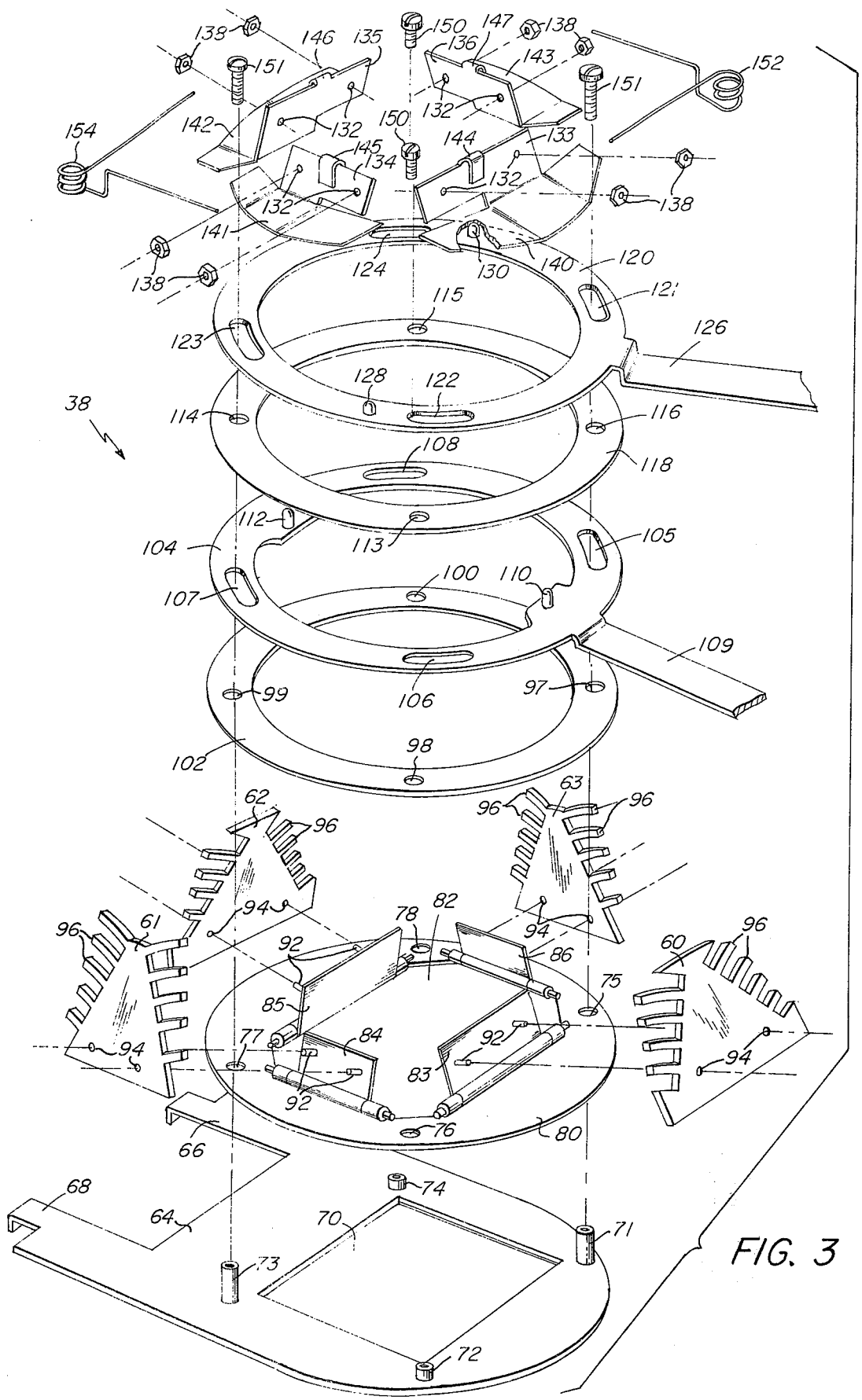
FIG. 3 is an exploded view of the radiation limiting device of this invention.

As shown in FIG. 3, the frusto-pyramidal shutter 38 may include a base plate 64 made of suitable material, such as aluminum, for example, and having flanged arm portions 66 and 68, respectively, which may be attached to a fixed support member (not shown) in housing 36. Extending through the base plate 64 is a substantially square opening 70 having corners located adjacent respective open-ended sleeves 71–74 which have opposing ends fixedly attached, as by welding, for example, to the base plate 64. The sleeves 71–74 are internally threaded and project outwardly from a flat surface of the base plate 64, the sleeves 71 and 73 being of greater length than the sleeves 72 and 74. Sleeves 71–74 extend through respective aligned apertures 75–78 which are marginally disposed in a circular disc 80 overlying the base plate 64. Disc 80 is made of a suitable material, such as aluminum, for example, and has extending through it a centrally disposed opening 82 which is axially aligned with the opening 70 in base plate 64.

Four frusto-triangular plates 60–63, respectively, are pivotally secured, as by respective hinge plates 83–86, for example, to edge portions of the disc 80 adjacent the opening 82. Each of the hinge plates 83–86 may be provided with a respective pair of outwardly extending bolts 92 which pass through aligned apertures 94 in the associated frusto-triangular plates. The frusto-triangular plates 60–63, respectively, are made of X-ray absorbent material, such as lead, for example, and are supported by the respective hinge plates 83–86, at an inclined angle with the axial centerline of opening 82. Each of the frusto-triangular plates 60–63 has sloped edge portions provided with a respective plurality of spaced arcuate teeth 96 which are concentrically disposed with respect to the associated base corner of the plate. As a result, the teeth 96 on each sloped edge portion intermesh with teeth 96 of adjacent plates 60–63, respectively, thereby forming the frusto-pyramidal structure.

The internally threaded sleeves 71–74 also extend through respective aligned apertures 97–100 in a ring 102 which is axially aligned with opening 82 and superimposed on the disc 80. Thus, ring 102 encircles the frusto-pyramidal structure formed by plates 60–63 and is made of a suitably smooth material, such as polyethylene, for example, which provides a bearing surface for an overlying rotatable ring 104 made of suitable material, such as aluminum, for example. Ring 104 is axially aligned with the opening 82 and has disposed therein four arcuate-shaped slots 105–108 through which the sleeves 71–74, respectively, extend. Projecting radially outward from the ring 104 is a fixedly attached arm 109 whereby the ring 104 may be rotated until the sleeves 71–74 butt against ends of the slots 105–108, respectively, depending on the direction of rotation. Opposing inner peripheral portions of the ring 104 extend radially inward and support respective studs 110 and 112 which convert the rotation of ring 104 into respective camming actions whereby the frusto-triangular plates 60 and 62, respectively, are pivoted in opposing directions relative to the axial centerline of opening 82.

The internally threaded sleeves 71–74 also extend through respective aligned apertures 113–116 in a ring 118 which is axially aligned with opening 82 and superimposed on the ring 104. Thus, ring 118 also encircles the frusto-pyramidal structure formed by plates 83–87, respectively, and is made of a suitably smooth material, such as polyethylene, for example, Ring 118 not only provides a bearing surface for the underlying rotatable ring 104 but also for an overlying rotatable ring 120 made of suitable material, such as aluminum, for example. The ring 120 is axially aligned with the opening 82 and has disposed therein four arcuate-shaped slots 121–124, respectively, through which respective sleeves 71–74 extend. Projecting radially outward from the ring 120 is a fixedly attached arm 126 whereby the ring 120 may be rotated until the sleeves 71–74 butt against ends of the slots 121–124, respectively, depending on the direction of rotation. Opposing arcuate portions of the ring 120 carry respective studs 128 and 130 which convert the rotation of ring 120 into respective camming actions. As a result, the frusto-triangular plates 61 and 63, respectively, are pivoted in opposing directions relative to the axial centerline of opening 82, independently of the frusto-triangular plates 60 and 62, respectively.

The bolts 92 extending from the respective hinge plates 83–86 and passing through aligned apertures 94 in the frusto-triangular plates 60–63, respectively, also pass through aligned apertures 132 in contiguous mounting flanges 133–136, respectively, and are threadingly engaged by respective hold-down nuts 138. The mounting flanges 133–136 are attached at right angles to respective sloped camming members 140–143 which overlie the studs 110, 128, 112 and 130 respectively. The mounting flanges 133–136 and the camming members 140–143 are made of suitable material, such as aluminum, for example. Each of the mounting flanges 133–136 is provided with a turned down tab portion, 144–147, respectively.

The sleeves 72 and 74 extending from the base plate 64 have open ends threadingly engaged by respective screws 150. The longer sleeves 71 and 73 have protruding open end portions which are encircled by respective coil springs 152 and 154, and are threadingly engaged by respective screws 151. The spring 152 has extended end portions clamped to respective frusto-triangular plates 60 and 63 by the associated tab portions 144 and 147, respectively. Similarly, the spring 154 has extended end portions clamped to respective frusto-triangular plates 61 and 62 by the associated tab portions 145 and 146, respectively. Thus, the springs 152 and 154 tend to resiliently pivot the frusto-triangular plates 60–63 away from the axial centerline of frusto-pyramidal shutter 38.

Figure 4:
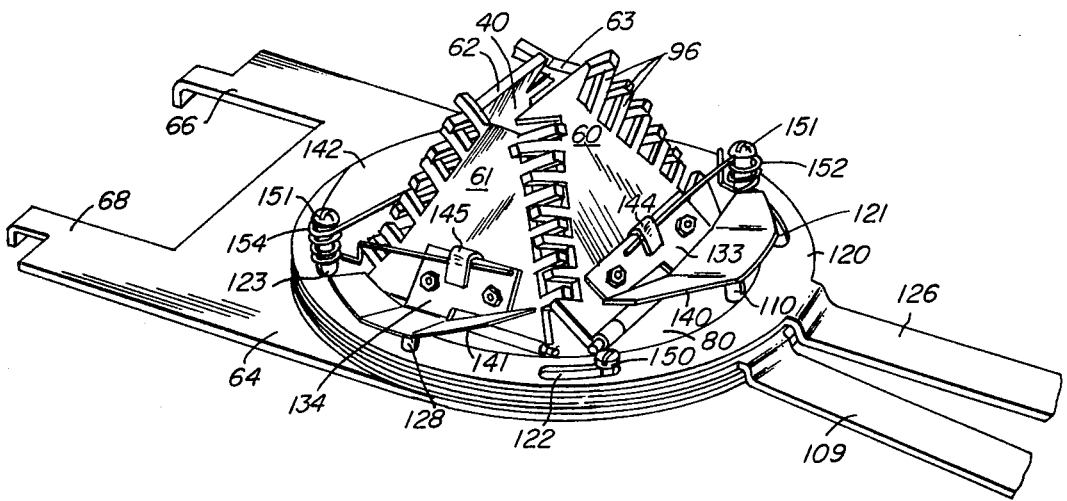
FIG. 4 is an isometric view of the radiation limiting device shown in FIG. 3 defining an adjusted entrance aperture.

As shown in FIG. 4, when the arm 109 is rotated such that the respective studs 110 and 112 are urged against the adjacent sloped surfaces of overlying camming members 140 and 142, respectively, the frusto-triangular plates 60 and 62 are pivoted toward the axial centerline of the frusto-pyramidal shutter 38. Accordingly, the teeth 96 on the sloped edges of plates 60 and 62 move arcuately relative to the adjacent sloped edges of frusto-triangular plates 61 and 63, respectively, and intermesh with the spaced teeth 96 thereof. Similarly, when the arm 126 is rotated such that the respective studs 128 and 130 are urged against the adjacent sloped surfaces of overlying camming members 141 and 143, respectively, the frusto-triangular plates 61 and 63 are pivoted toward the axial centerline of the frusto-pyramidal shutter 38. As a result, the corresponding dimensions of the entrance aperture 36 are reduced accordingly.

Figure 5:
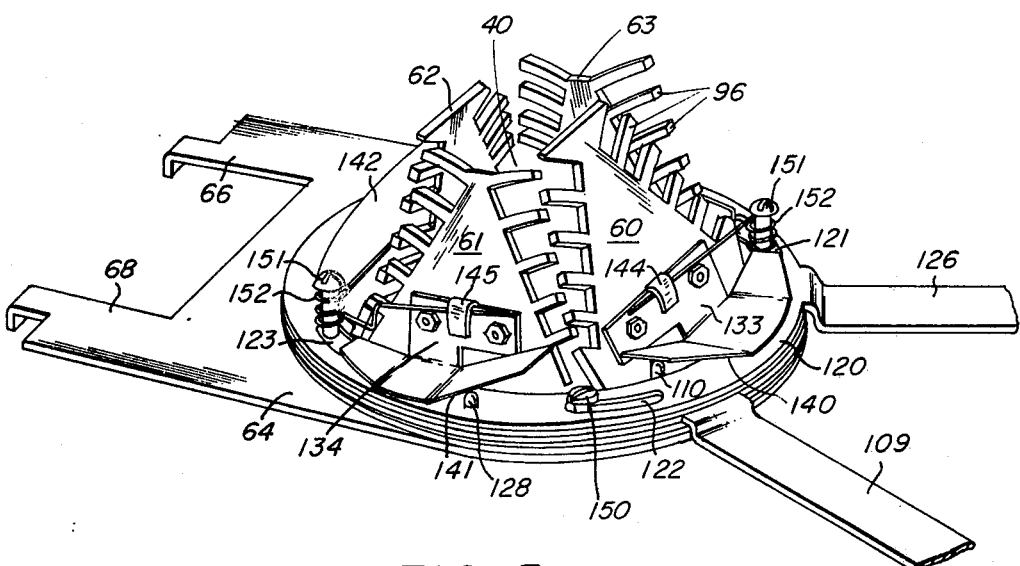
FIG. 5 is an isometric view of the radiation limiting device shown in FIG. 4 defining a fully open entrance aperture.

However, the entrance aperture 36 is closed down, as described, against the resilient pressure exerted by springs 152 and 154, respectively. Consequently, as shown in FIG. 5, when the arm 104 is rotated in the reverse direction, the springs 152 and 154 pivot the frusto-triangular plates 60 and 63, respectively, away from the axial centerline of the frusto-pyramidal shutter 38. Similarly, when the arm 126 is rotated in the reverse direction, the springs 152 and 154 pivot the frusto-triangular plates 63 and 61, respectively away from the axial centerline of the frusto-pyramidal shutter 38. As a result, the corresponding dimensions of the entrance aperture 36 are increased and the aperture 36 is opened accordingly.

From the foregoing, it will be apparent that all of the objectives of this invention have been achieved by the structures shown and described herein. It will be also apparent, however, that various changes may be made by those skilled in the art without departing from the spirit of the invention as expressed in the appended claims. It is to be understood, therefore, all matter shown and described herein is to be interpreted as illustrative and not in a limiting sense.

What is claimed is:

1. An off-focus X-radiation limiting device comprising:
    a hollow frusto-pyramidal shutter having frusto-triangular walls made of X-radiation absorbent material and having pivotal means secured to the base portions thereof for permitting movement of the opposing end portions relative to the axial centerline of the structure to define a radiation limiting aperture;
    each of the walls being a frusto-triangular plate having respective pluralities of spaced teeth arcuately disposed on the sloped edges thereof and substantially concentric in the plane of the plate with the aligned base corner thereof for intermeshing with similarly disposed teeth on respective sloped edges of adjacent frusto-triangular walls of the shutter; and
    means for controllably pivoting the walls relative to the axial centerline of the shutter to vary the size of the aperture.

2. A radiation limiting shutter as set forth in claim 1 wherein the means for controllably pivoting the walls includes resilient means for pivoting the frusto-triangular plates relative to the axial centerline of the shutter.

3. A radiation limiting shutter as set forth in claim 2 wherein the means for controllably pivoting the walls includes camming means for pivoting the frusto-triangular plates relative to the axial centerline of the shutter.

4. An X-radiation collimating device comprising:
a housing;
an off-Focus X-radiation limiting shutter including a hollow frusto-pyramidal structure extended externally from a wall of the housing and having four X-radiation absorbent, frusto-triangular walls pivotally supported adjacent the base portions thereof for moving the opposing end portions relative to the axial centerline of the structure to define a rectangular entrance aperture,
each of the walls being a frusto-triangular plate having respective pluralities of spaced teeth arcuately disposed on the sloped edges thereof and substantially concentric in the plane of the plate with the aligned base corner thereof for intermeshing with similarly disposed teeth on respective sloped edges of adjacent walls of the shutter;
means for controllably pivoting the frusto-triangular walls relative to the axial centerline of the structure to vary the size of the entrance aperture; and
a beam collimating shutter within the housing and having a plurality of on-focus X-radiation absorbent elements movably supported to define an X-ray beam collimating aperture.

5. A radiation collimating device as set forth in claim 4 wherein the respective pluralities of spaced teeth are substantially concentric with aligned base corners of the associated frusto-triangular plates.

6. A radiation collimating device as set forth in claim 4 wherein the plurality of X-radiation absorbent elements comprises two orthogonally disposed pairs of opposing pivoted plates, each disposed in registration with a respective one of the frusto-triangular plates.

7. A radiation collimating device as set forth in claim 6 wherein the controllable moving means include means for moving the frusto-triangular plates in accordance with movement of the corresponding beam collimating plates.

8. In combination:
a housing having an X-radiation transparent port recessed in a wall portion thereof;
an X-radiation source within the housing and disposed to direct a beam of radiation through the port;
an off-focus radiation limiting shutter including a frusto-pyramidal structure mounted externally over the port and having X-radiation absorbent, frusto-triangular walls extended into the recessed area of the port and pivotally supported adjacent the base portions thereof for moving the opposing end portions relative to axial centerline of the structure to define an X-radiation limiting aperture adjacent the source,
each of the walls being a frusto-triangular plate having respective pluralities of spaced teeth arcuately disposed on the sloped edges thereof and substantially concentric in the plane of the plate with the aligned base corner thereof for intermeshing with similarly disposed teeth on respective sloped edges of adjacent frusto-trianglular walls of the structure; and
means operatively connected to the walls for controllably pivoting the walls relative to the axial centerline of the structure to vary the size of the aperture.

9. The combination as set forth in claim 8 wherein the arcuate teeth are substantially concentric with respect to the aligned base corner of the associated frusto-triangular plate.

10. The combination as set forth in claim 9 wherein the moving means includes camming means for pivoting the frusto-triangular plates in one direction relative to the axial centerline of the shutter and resilient means for pivoting the frusto-triangular plates in the opposing direction.

* * * * *